(12) United States Patent
Tamarindo (10) Patent No.: US 10,588,990 B2
(45) Date of Patent: Mar. 17, 2020

(54) SYSTEM FOR HANDLING STERILIZATION OF THIN BODY FLEXIBLE CONTAINERS (POUCH)

(71) Applicant: GUALA PACK S.p.A., Castellazzo Bormida, Alessandria (IT)

(72) Inventor: Stefano Tamarindo, Alessandria (IT)

(73) Assignee: GUALA PACK S.p.A., Castellazzo Bormida, Alessandria (IT)

( * ) Notice: Subject to any disclaimer, the term of this patent is extended or adjusted under 35 U.S.C. 154(b) by 192 days.

(21) Appl. No.: 15/739,947

(22) PCT Filed: Feb. 29, 2016

(86) PCT No.: PCT/IB2016/051108
§ 371 (c)(1),
(2) Date: Dec. 26, 2017

(87) PCT Pub. No.: WO2017/001947
PCT Pub. Date: Jan. 5, 2017

(65) Prior Publication Data
US 2018/0185528 A1    Jul. 5, 2018

(30) Foreign Application Priority Data

Jul. 1, 2015  (IT) .......................... 102015000029638

(51) Int. Cl.
*B65B 55/08* (2006.01)
*A61L 2/08* (2006.01)
(Continued)

(52) U.S. Cl.
CPC .............. *A61L 2/087* (2013.01); *B65B 3/045* (2013.01); *B65B 5/06* (2013.01); *B65B 5/10* (2013.01);
(Continued)

(58) Field of Classification Search
CPC ....... A61L 2/087; B65B 3/022; B65B 51/046; B65B 55/02; B65B 55/08
(Continued)

(56) References Cited

U.S. PATENT DOCUMENTS 4,794,750 A * 1/1989 Schmidt .................... A61J 1/10
264/138
5,843,374 A * 12/1998 Sizer ........................ A23L 3/28
422/24
(Continued)

FOREIGN PATENT DOCUMENTS

DE    10 2005 017 404 A1    10/2006
DE    10 2010 049 263 A1    4/2012
(Continued)

OTHER PUBLICATIONS

International Search Report and Written Opinion of the International Searching Authority for corresponding International Patent Application No. PCT/IB2016/051108 dated May 30, 2016, 9 pages.
(Continued)

*Primary Examiner* — Gloria R Weeks
(74) *Attorney, Agent, or Firm* — Merchant & Gould P.C.

(57) ABSTRACT

A system handles the sterilization of thin-body, pouch-type, flexible containers (1) and provides for applying sacrificial closures (200) to the pouches. The system loads the provisional closed pouches to be sterilized on a transport device (300) for collective transport, to perform the sterilization of the transport device (300) carrying the provisional closed pouches. The system separates in a sterile chamber, the sacrificial closures (200) from the pouches, performing filling and applying an inviolable cap (100).

17 Claims, 5 Drawing Sheets

(51) Int. Cl.
  *B67C 7/00* (2006.01)
  *B65B 61/18* (2006.01)
  *B65B 3/04* (2006.01)
  *B65B 43/12* (2006.01)
  *B65B 5/06* (2006.01)
  *B65B 5/10* (2006.01)
  *B65B 7/02* (2006.01)
  *B65B 61/20* (2006.01)

(52) U.S. Cl.
  CPC .............. *B65B 7/02* (2013.01); *B65B 43/123* (2013.01); *B65B 55/08* (2013.01); *B65B 61/186* (2013.01); *B65B 61/20* (2013.01); *B67C 7/008* (2013.01); *A61L 2202/11* (2013.01); *A61L 2202/23* (2013.01)

(58) Field of Classification Search
  USPC .................................................. 53/425, 426
  See application file for complete search history.

(56) References Cited

U.S. PATENT DOCUMENTS

| | | | | |
|---|---|---|---|---|
| 6,629,401 B1* | 10/2003 | Hins | ..................... | B65B 7/2892 53/425 |
| 8,733,600 B2* | 5/2014 | Pritchard | ............. | B65D 47/103 222/494 |
| 8,863,790 B2* | 10/2014 | Ziegler | ................... | A61L 2/087 141/11 |
| 9,321,052 B2* | 4/2016 | Coleman | .................. | G01N 1/10 |
| 9,782,502 B2* | 10/2017 | Laguzzi | .................. | A61L 2/087 |
| 10,265,737 B2* | 4/2019 | Fitzgerald | ............... | B08B 3/041 |
| 2008/0072542 A1* | 3/2008 | Levati | ................... | B65B 31/024 53/426 |
| 2010/0005760 A1* | 1/2010 | Matheyka | ............... | B65B 55/08 53/426 |
| 2015/0059288 A1* | 3/2015 | Wu | ....................... | B65B 55/027 53/426 |
| 2015/0121807 A1* | 5/2015 | Taber | .................... | B65B 31/006 53/431 |
| 2016/0145025 A1* | 5/2016 | Van Der Molen | .......................... | B65D 75/5883 222/107 |

FOREIGN PATENT DOCUMENTS

| | | |
|---|---|---|
| EP | 2 701 979 B1 | 7/2015 |
| EP | 2 701 751 B1 | 8/2016 |
| JP | 2003-237742 A | 8/2003 |
| JP | 2006-248562 A | 9/2006 |
| JP | 4826733 A | 11/2011 |
| JP | 2013-086809 A | 5/2013 |
| JP | 2014-128254 A | 7/2014 |
| WO | 2014/171814 A1 | 10/2014 |
| WO | WO 2014171814 * 10/2014 ............... B65B 5/06 |

OTHER PUBLICATIONS

Chinese Office Action for corresponding Chinese Patent Application No. 201680038266.2 dated Apr. 23, 2019, 14 pages.

* cited by examiner

SYSTEM FOR HANDLING STERILIZATION OF THIN BODY FLEXIBLE CONTAINERS (POUCH)

This application is a National Stage Application of PCT/M2016/051108, filed 29 Feb. 2016, which claims benefit of Serial No. 10/2015000029638, filed 1 Jul. 2015, and which applications are incorporated herein by reference. To the extent appropriate, a claim of priority is made to each of the above disclosed applications.

BACKGROUND OF THE INVENTION

This invention relates to a method and an apparatus for the preparation for sterilisation of thin-body flexible containers (generally known as "pouches"). These containers are typically used to contain food products such as fruit juices, yoghurt, fruit or vegetable purée, creams, honey and the like, or medicines, and the like.

In the food industry, the sterilisation of this type of container has enormous importance for the prevention of infections and the correct preservation of the food contained in it.

Sometimes, a chemical sterilisation is performed, during which the container is washed with disinfectants, for example hydrogen peroxide, and then dried, before being sent to subsequent filling.

However, chemical sterilisation has some disadvantages such as, for example, the presence of disinfectant residues in the dry container or the presence of areas not disinfected due to complex geometries or irregularities of the container. This disadvantage is particularly felt precisely in the pouch industry.

While, sterilisation by ionising radiation, such as gamma rays or electron beams, is very widespread. For example, the Applicant is the holder of patents EP 2701751 and EP 2701979, relating to electron-beam sterilisation systems.

Usually, sterilisation using ionising radiation is carried out in specialised centres, to which the producer subject of the containers sends them to be treated; after sterilisation, sterile containers are sent to the company who fills and closes them, using techniques that allow maintaining sterile conditions inside the container. These logistics obviously imply considerable transport costs between the sites and a significant management complexity of the containers within the sites themselves.

SUMMARY OF THE INVENTION

The purpose of this invention is to provide a method and an apparatus for the preparation for sterilisation of flexible containers, which are able to reduce the impact of such costs, allowing for the management of a high number of containers simultaneously.

BRIEF DESCRIPTION OF THE DRAWINGS

The characteristics and advantages of this invention will be apparent from the following description, given by way of non-limiting example, in accordance with the accompanying figures, in which.

DETAILED DESCRIPTION OF THE DRAWINGS

With reference to the attached drawings, reference number 1 indicates a flexible, thin-body, pouch-type container as a whole.

Figure 1:
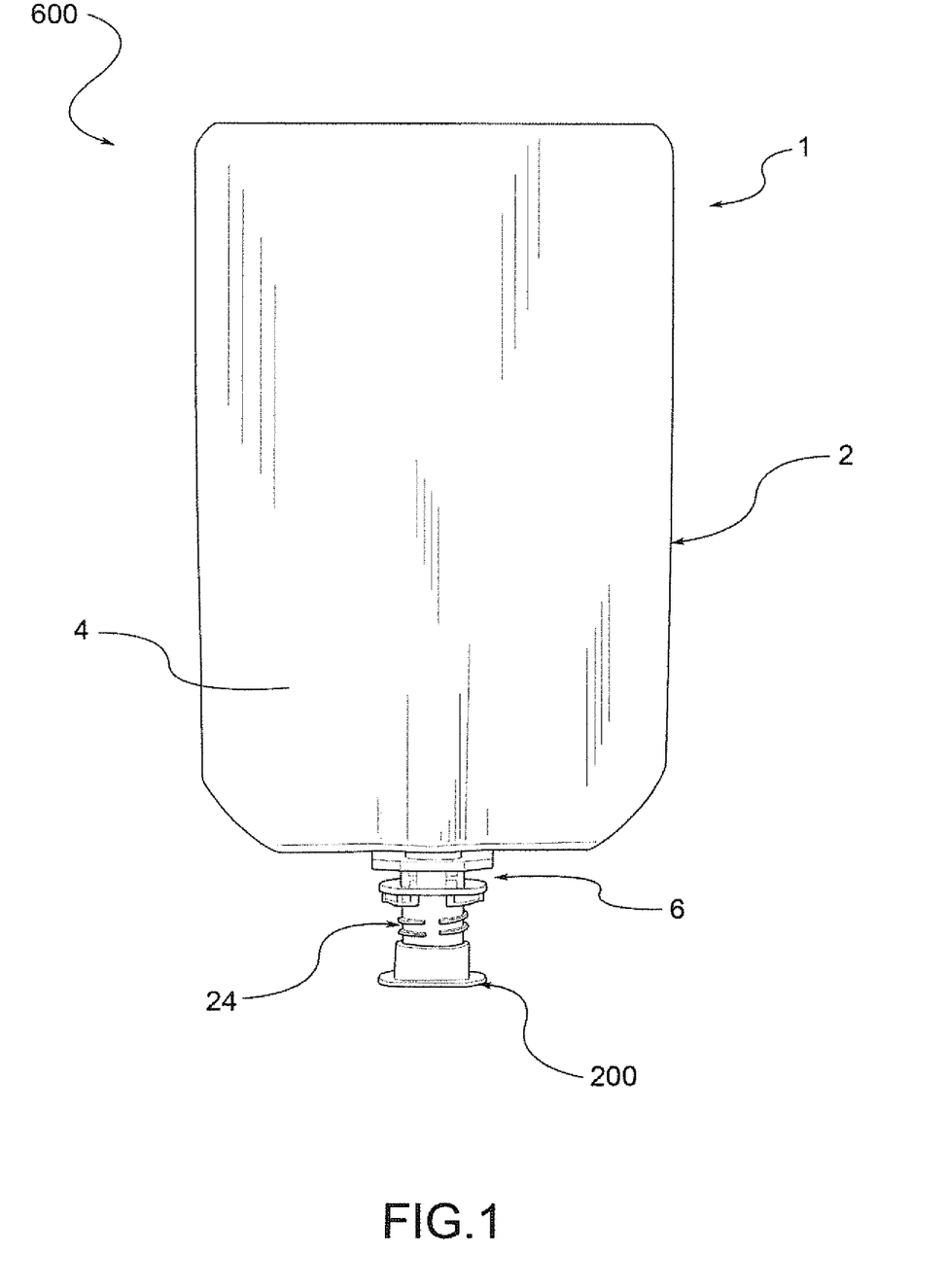
FIG. 1 shows a flexible, thin-body, pouch-type container provided with a sacrificial closure.

The pouch 1 comprises a container body 2 formed by two or more walls 4 consisting of flexible film, facing each other and joined, for example welded, along the edges, possibly with folding lateral walls (gussets) or with a bottom wall.

According to an embodiment, the film is a single layer. Preferably, the film is multilayer.

Preferably, one or more layers of the film are made from polymers, such as polyolefins, polyamides, polyesters, polycarbonates, polymers derived from renewable sources (bio-based), bio-degradable and compostable.

Preferably, also, one or more layers are coated with metal oxides, for example aluminium oxides, silicon or combinations thereof, or with lacquers, with or without the presence of metal oxides, such as aluminium oxides.

Preferably, also, one or more layers are impermeable to oxygen, moisture and/or light.

Preferably, also, the film is suitable to withstand sterilisation treatments using ionising radiation, as well as some heat treatments such as pasteurisation, freezing, or treatments under pressure or under vacuum.

Preferably, also, the films or individual layers have a thickness between a few nanometres and a few millimetres.

The pouch 1 further comprises a spout 6 made of rigid material, sealingly applied to the body 2. In particular, the spout 6 is typically inserted into a portion of the edge of the body 2, usually between the lateral walls 4.

Preferably, the spout 6 is made, in a single piece, of plastic, for example polyethylene or polypropylene, by injection moulding.

The spout 6 extends substantially along a longitudinal axis Z and comprises, from the part that remains inside the container body 2 of the pouch 1 towards the outside, an entrance portion 8, an intermediate portion 10 and a final portion 12.

Figure 3:
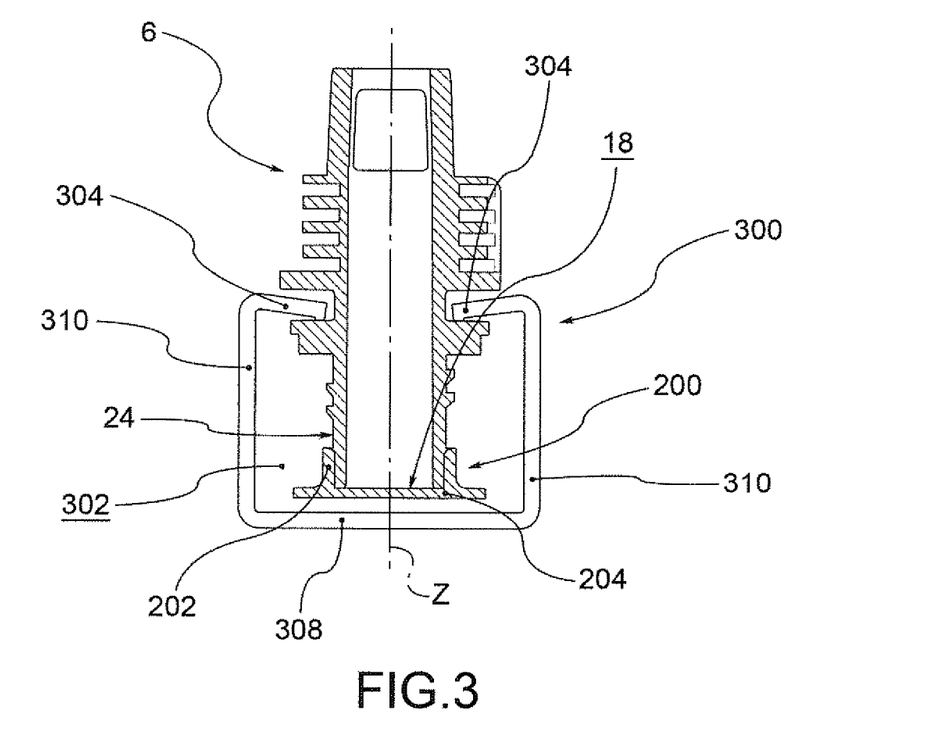
FIG. 3 is a sectional view of a drinking spout provided with the sacrificial closure, partially housed in the transport device, realised according to a first sectional plane, orthogonal to an axis X in FIG. 2.
Figure 4:
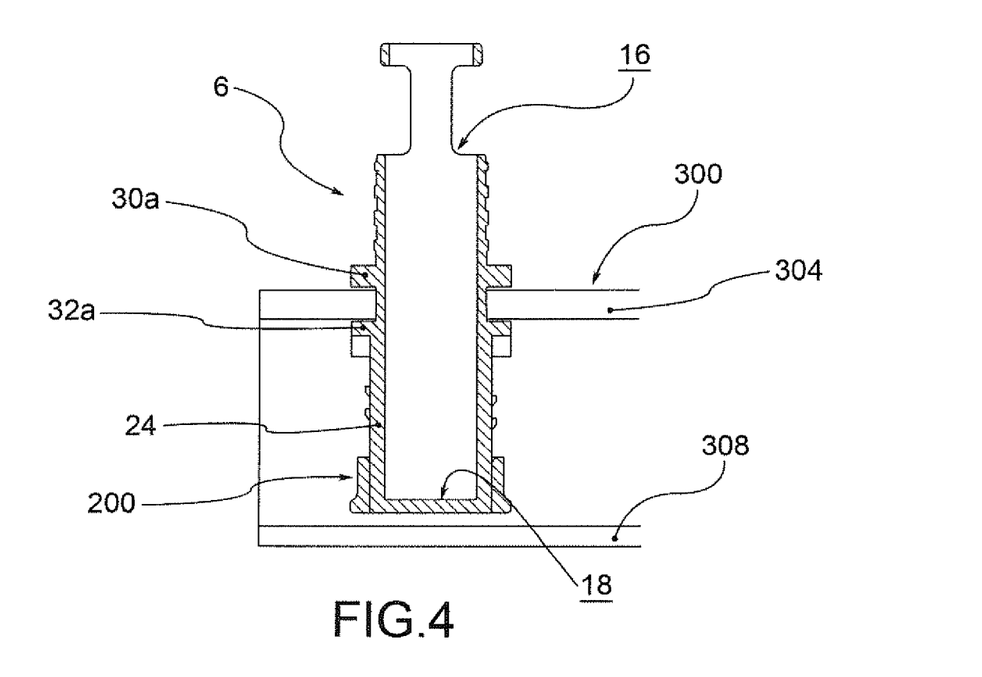
FIG. 4 is a sectional view of the drinking spout provided with the sacrificial closure, partially housed in the transport device, realised according to a first sectional plane, containing the axis X in FIG. 2 and orthogonal to the first sectional plane.

Internally, the spout 6 comprises a conduit 14, usually of a circular cylindrical shape, that extends along the longitudinal axis Z, between an inlet 16 of the entrance portion 8 and an outlet mouth 18 of the final portion 12.

The entrance portion 8 is preferably formed by a pair of facing walls 20, with prevailing extension in the transverse direction, i.e., perpendicular to the longitudinal axis Z, joined at the ends. These walls form two outwardly engaging surfaces 22 intended for coupling with the films of the container body 2, preferably by means of welding.

Figure 5:
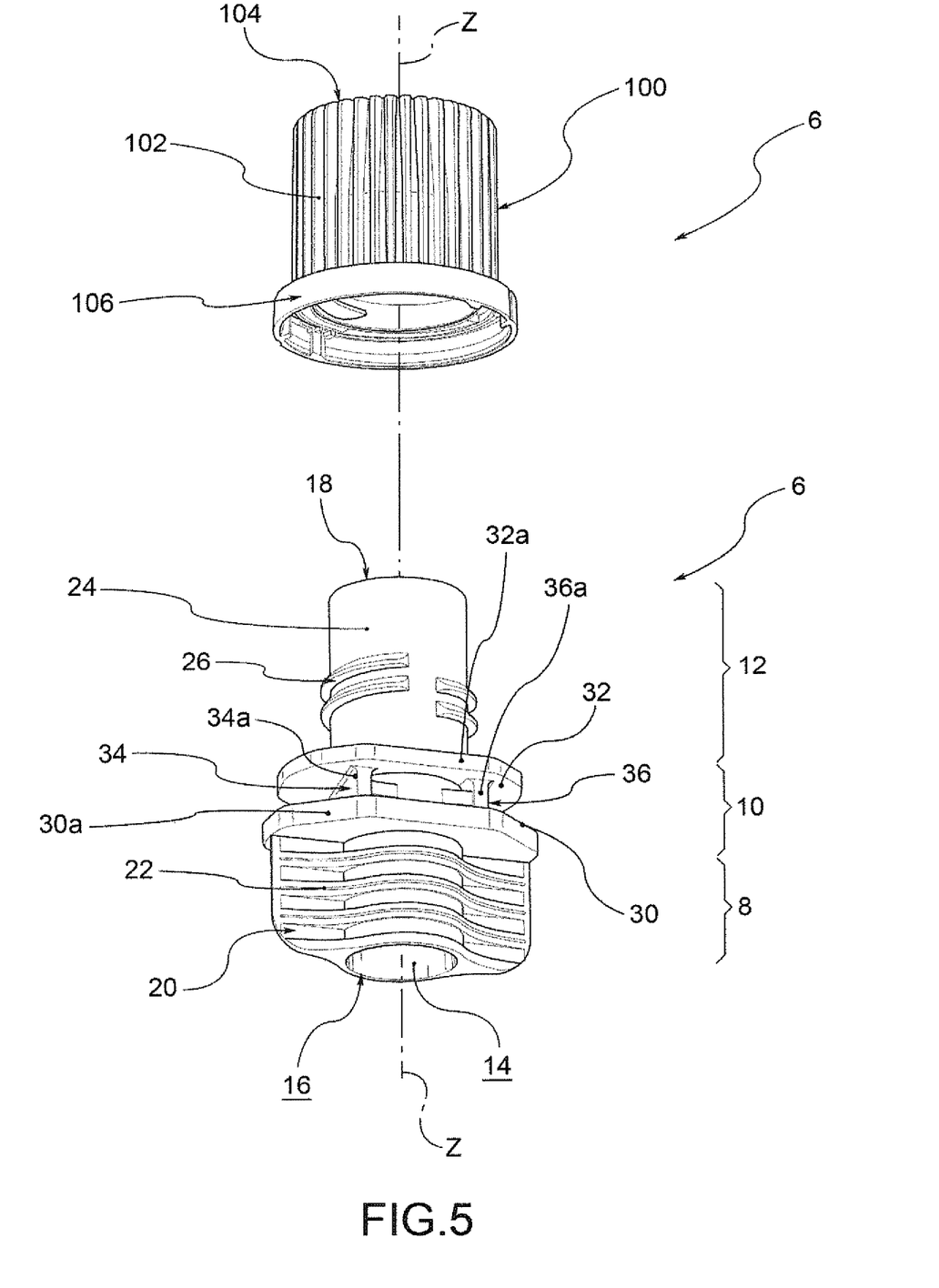
FIG. 5 shows a spout and a final cap applicable to the spout, in separate parts.

The final portion 12 comprises a tube 24, which extends along the longitudinal axis Z, coaxial with the conduit 14, typically terminating with the outlet mouth 18.

According to an embodiment, the final portion 12 further comprises a threading 26 for screwing a cap 100, realised, for example, by sections of interrupted threading.

Preferably, the cap 100 for the spout 6 comprises an outer annular wall 102, which surrounds the tube 24 and, for example, is provided with threading for engagement with the threading 26 of the spout 6.

At one end of the outer annular wall 102, the cap 100 further comprises a bottom 104 suitable to close the outlet mouth 18 and, at the other end, a tamper-evident seal 106.

Preferably, the final portion 12 of the spout 106 comprises an engaging portion suitable to engage with the tamper-evident seal 106 of the cap 100, to realise an anti-rotation constraint of said tamper-evident seal.

In other words, the cap 100 is applicable to the spout 6 in an inviolable manner, since the unscrewing of the cap causes the tearing of the tamper-evident seal 106, which engages with the engaging portion 6 of the spout.

Furthermore, according to the invention, there is provided a sacrificial closure 200 suitable to be applied to the spout 6, and in particular to the tube 24 of the final portion 12, to close the outlet mouth 18, in a reversible manner.

For example, the sacrificial closure 200 comprises a lateral annular wall 202 that, applied to the closure to the spout 6, extends along the longitudinal axis Z, and a bottom 204, for example made in one piece with the lateral wall 202, for the closure of the outlet mouth 18.

The sacrificial closure 200 is sealingly applicable to the tube 24 of the spout 6, so as to preserve any pre-existing conditions of sterility inside the pouch.

In addition, the sacrificial closure 200 is reversibly applicable to the tube 24 of the spout 6, i.e., in such a way that it is separable from the spout without tears or breaks.

For example, the sacrificial closure 6 is pressure-applicable to the tube 24 of the spout 6, for example in such a way that the lateral wall 202 surrounds the wall of the tube 24 and sealingly engages with it.

The intermediate portion 10 comprises a first support surface 30 and a second support surface 32, lying substantially on planes orthogonal to the longitudinal axis Z and spaced axially.

For example, said support surfaces are constituted by the facing surfaces of a first plate 30a and a second plate 32a, respectively, spaced axially.

Preferably, the first plate 30a is joined to the walls 20 of the entrance portion 8, while the second plate 32a is joined to the engaging portion of the final portion 12.

Preferably, moreover, the intermediate portion 10 has a first guide surface 34 and a second guide surface 36, mutually parallel, parallel to the longitudinal axis Z and equally spaced from this, contained between the support surfaces 30,32.

For example, said guide surfaces are constituted by the facing surfaces of guide walls 34a,36a respectively, spaced transversely.

Figure 2:
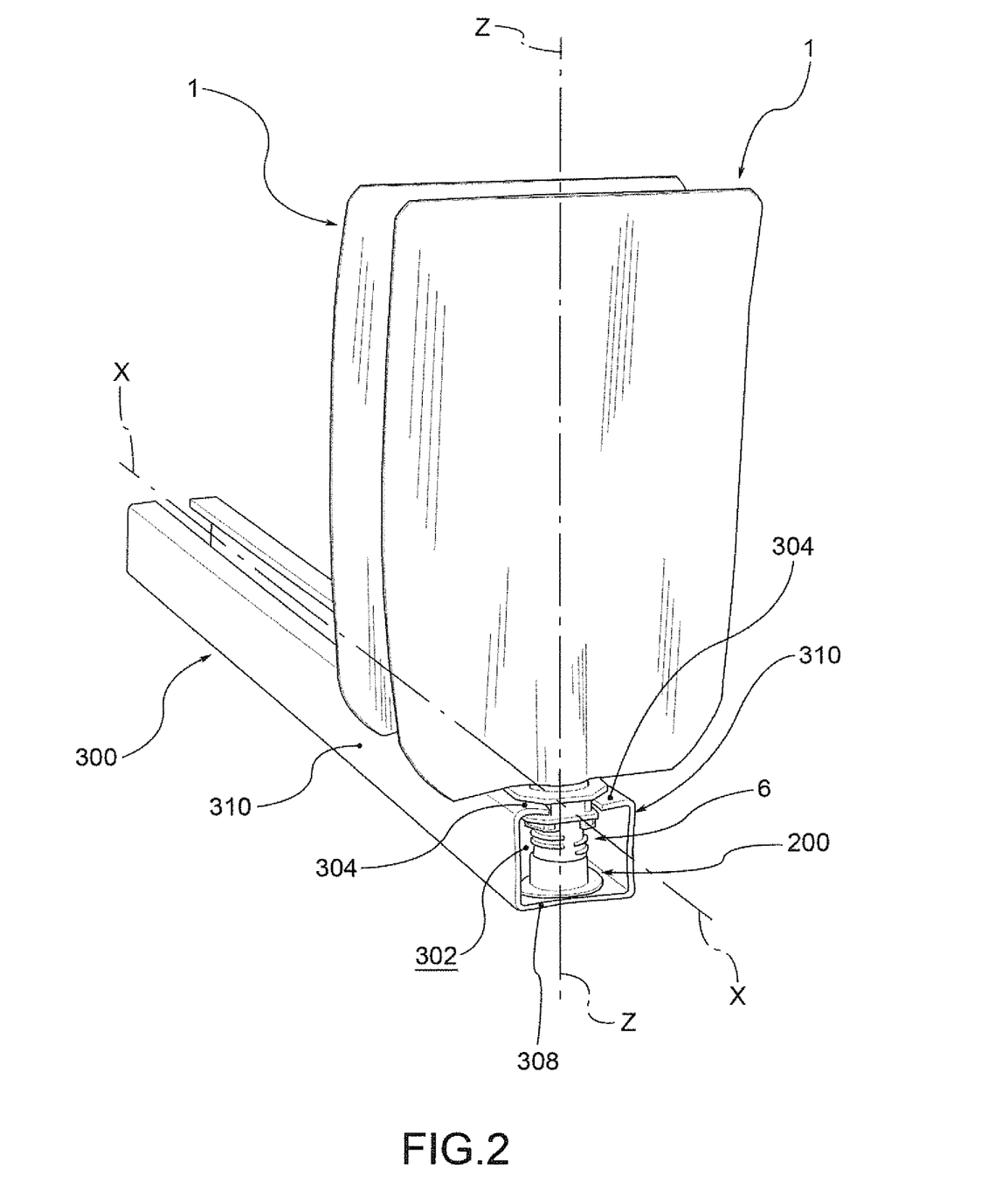
FIG. 2 illustrates a plurality of containers of FIG. 1, loaded on a transport device.

According to the invention, there is also provided a transport device 300 suitable for loading a plurality of pouches 1 provided with the respective sacrificial closure 200.

Said transport device 300 has a compartment 302 in which, when the pouch with the closure is loaded, at least a portion of the spout 6 and the respective sacrificial closure 200 applied to the spout is received, while any remaining part of the spout 6 and the container body 2 are arranged outside the compartment 302.

In addition, the transport device 300 has support means suitable for engaging the spout 6 and supporting the pouch provided with the closure, both in the "standing" configuration, in which the spout is arranged above and the pouch below, and the "upside down" configuration, in which the spout is arranged below and the pouch above (FIG. 2).

Preferably, said support means comprise a pair of fins 304 suitable to be received between the support surfaces 30,32 of the spout 6, creating a bilateral engagement in the direction of the longitudinal axis Z.

In addition, said engagement means of the transport device 300 are suitable to slidingly engage the spout 6 along a sliding axis X, lying on a plane orthogonal to the longitudinal axis Z.

In particular, said fins 304 allow the pouch to slide with the closure along the sliding axis X; preferably, said sliding is guided by the guide surfaces 34,36 that cooperate with the fins 304.

According to a preferred embodiment, said transport device 300 comprises a section bar having extension along said sliding axis X.

Preferably, said section bar comprises a base 308, flanked by lateral walls 310, surmounted by said fins 304, each projecting from the respective lateral wall 310. The base 308, the lateral walls 310 and the fins 304 peripherally define the compartment 302.

For example, after the pouch 1 with spout 6 is loaded on the section bar, the fins 304 are inserted between the support surfaces 30,32, while the second plate 32a, the tube 24 and the closure 200 are contained in the compartment 302.

According to the invention, a preparation method for sterilisation comprises a first step that involves the production of a plurality of container bodies 2, the production of a plurality of spouts 6 and the production (or reuse) of a plurality of sacrificial closures 200.

The spout 6 is sealingly applied to the respective container body 2, obtaining a plurality of pouches 1. The sacrificial closure 200 is applied, for example by pressure, to the tube 24, realising a provisional closed pouch to be sterilised 600.

In addition, the preparation method for sterilisation comprises a subsequent step of loading a plurality of transport devices 300 with provisional closed pouches to be sterilised, each transport device being loaded with a predetermined number of provisional closed pouches to be sterilised, for collective transport to a sterilising subject.

For example, the loading step involves the insertion by sliding of the provisional closed pouches 600 in said section bar along said sliding axis X and the support of the provisional closed pouch, in the "standing" or "upside down" configuration through the use of the fins 304 between the support surfaces 30,32 of the spouts 6.

Subsequently, preferably, the method involves forming a transport group 400, containing a plurality of transport devices 300, each carrying the closed pouches to be sterilised, stacked.

According to an embodiment (FIG. 6), the group 400 comprises a plurality of simple transport surfaces 402, wherein each transport surface 402 comprises a predefined number of transport devices 300 placed side by side at the same height, all carrying the provisional pouches arranged in the same direction, for example all "standing" or all "upside down". The transport surfaces 402 are stacked on each other, forming the transport group 400.

According to a further embodiment (FIG. 7), the group 400 comprises a plurality of dual transport surfaces 402, wherein each transport surface comprises a first level 404 comprising a predefined number of transport devices 300 placed side by side at the same height, all carrying the provisional pouches arranged in the same direction, for example all "standing" or all "upside down", and a second level 406 superimposed on the first, comprising a predefined number of transport devices 300 placed side by side and all carrying the provisional pouches arranged in the direction opposite to that of the first level 404, for example all "upside down" or all "standing".

Figures 6, 7:
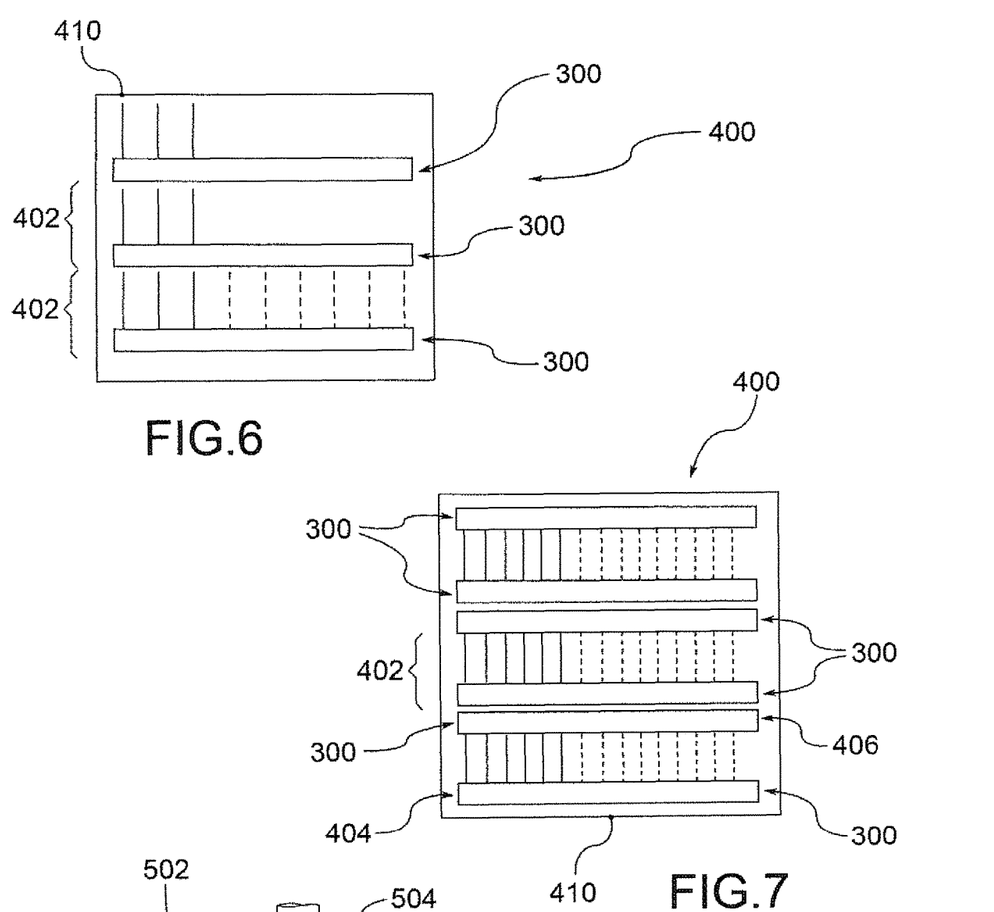
FIGS. 6 and 7 illustrate diagrams of construction variants of transport groups.

In the transportation surfaces according to this embodiment, the provisional "standing" pouches thus alternate with provisional "upside down" pouches along the sliding axis X.

Even said transport surfaces 402 are stacked on each other, forming the transport group 400.

The loading operations for the formation of the dual transport surfaces are illustrated, for pouches not provided with sacrificial closure, in European patent EP-B1-2611704 in the Applicant's name, whose teachings in this connection are incorporated here.

Generally, the transport group 400 is accommodated in a box 410, for example made of cardboard, for transport.

The method also provides for a possible transport step in which the transport group 400 is transported from the site of the producer subject to a steriliser subject, for example a specialised centre, or a filler subject that also performs sterilisation, where a sterilisation step is performed.

During the sterilisation step, entire transport group 400, whether or not provided with the box 410, or the individual transport surfaces 402 of this, simple or radiation.

If the sterilisation step took place in a specialised centre, the transport group 400, constituted by sterilised provisional closed pouches, is transport to the filler subject.

Figure 8:
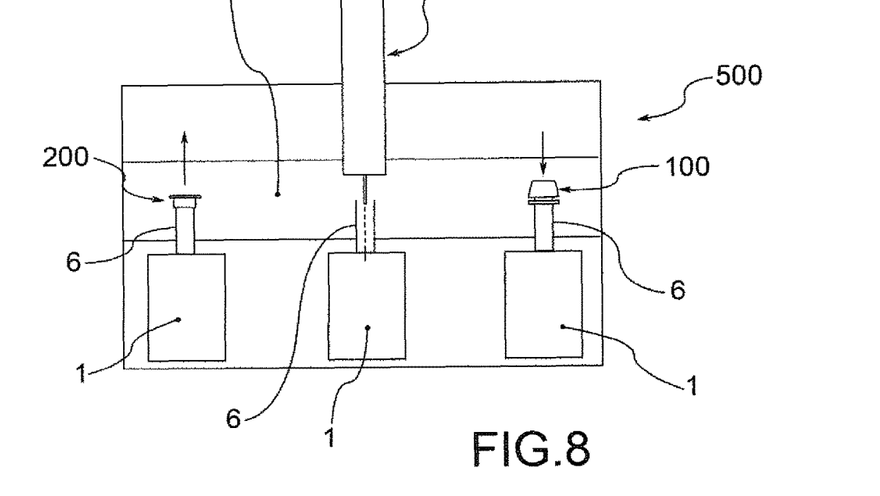
FIG. 8 is a diagram of a filling machine.

At the subject filler, the sterilised provisional closed pouches are picked from the transport group 400 and sent to a filling machine 500 provided with a sterile chamber 502 suitable to contain, for each sterilised provisional closed pouch, at least a portion of the tube 24 of the spout 6 and the sacrificial closing 200 applied to it.

In the sterile chamber 502 of the machine 500, there is a step of separation of the sacrificial closure 200 from the tube 24, so as to free the access to the outlet mouth 18 of the spout 6.

The sacrificial 200 closures are collected and set aside, and possibly sent for recycling.

The filling machine 500 further comprises filling means 504 that open into the sterile chamber 502, suitable for supplying on command the product to be filled in the pouch 1 through the spout 6. Therefore, there is a filling step.

Finally, in the sterile chamber 502 of the machine 500, there is a step of applying the inviolable cap 100 to the tube 24 of the spout 6.

The final closed pouches thus obtained, still sterile, provided with the cap 100 exit from the sterile chamber 502 and are sent to the subsequent packaging and shipping operations.

Innovatively, the sterilisation management system according to this invention overcomes the drawbacks of the known art, since it allows transporting or handling a large number of pouches, maintaining sterile conditions up to the application of the final cap.

It is clear that one skilled in the art, in order to meet contingent needs, may make changes to the method and device described above, all contained within the scope of protection defined by the claims.

The invention claimed is:

1. A method of preparation for sterilisation of pouches comprising the steps of:
producing a plurality of pouches, wherein each pouch comprises a container body formed by walls made of flexible film and a straw comprising an entrance portion with an inlet and a tube with an outlet, said straw being sealingly applied to the container body with at least a section of the tube protruding outside of the container body;
providing a plurality of sacrificial closures reversibly applicable to an outlet mouth of the straw;
applying, sealingly and reversibly, one of the sacrificial closures to the outlet of the straw, obtaining provisional non-filled closed pouches to be sterilised, wherein the one of the sacrificial closures is sealingly applied to the outlet to preserve a future condition of sterility inside the pouch;
loading a plurality of provisional closed pouches to be sterilised on a transport device for collective transport towards a steriliser.

2. The method according to claim 1, wherein the transport device consists of a section bar having a prevailing extension along a sliding axis and the loading step involves insertion by sliding of the provisional closed pouches in said section bar along said sliding axis.

3. The method according to claim 1, wherein the transport device comprises fins and the loading step provides for support of the provisional closed pouch, in a standing configuration, in which the straw is arranged above and the pouch below, or in an upside down configuration, in which the straw is arranged below and the pouch above, through use of the fins between the support surfaces of the straws.

4. The method according to claim 1, wherein after the step of loading the provisional closed pouches to be sterilised on the transport device, further comprising a step of forming a transport group containing a plurality of stacked transport devices.

5. The method according to claim 1, wherein each sacrificial closure is applied by pressure to the outlet.

6. The method according to claim 1, wherein each sacrificial closure comprises a lateral annular wall and a bottom, made in one piece with the lateral wall, for the closure of the outlet.

7. A method of sterilisation of flexible pouches, comprising the steps of:
providing a transport group comprising a plurality of transport devices, each of the transport devices carrying non-filled closed pouches to be sterilised and stacked; wherein each closed pouch to be sterilised comprises a container body having walls made of film, a straw sealingly applied to the container body and a sacrificial closure sealingly and reversibly applied to an inlet of a tube of the straw to close the tube, wherein the sacrificial closure is sealingly applied to the outlet to preserve a future condition of sterility inside the pouch;
performing a sterilisation of the transport group by ionising radiation.

8. A method for filling flexible pouches, comprising the steps of:
providing a transport group comprising a plurality of transport devices, each carrying sterilized closed non-filled pouches, the transport devices being stacked, wherein each closed pouch comprises a container body having walls made of film, a straw sealingly applied to the container body and a sacrificial closure sealingly and reversibly applied to an inlet of a tube of the straw to close the tube, wherein the sacrificial closure is sealingly applied to the outlet so as to preserve a condition of sterility inside the pouch;

picking the closed pouches from the transport group and sending the closed pouches in succession to a sterile chamber;

for each sterilised closed pouch, making at least a portion of the tube provided with the sacrificial closure to pass through the sterile chamber;

during said passing through of the sterile chamber, separating the sacrificial closure from the tube, filling the sterilised open pouch and applying a tamper-proof cap to the tube to close the pouch.

9. A method for sterilising and filling flexible pouches, comprising the steps of:

producing a plurality of pouches, wherein each pouch comprises a container body formed by walls made of flexible film and a straw comprising an entrance portion with an inlet and a tube with an outlet, said straw being sealingly applied to the container body with at least a section of the tube protruding outside of the container body;

providing a plurality of sacrificial closures reversibly applicable to the outlet mouth of the straw;

applying one of the sacrificial closures to the outlet of the straw, thereby obtaining provisional closed non-filled pouches to be sterilised, wherein the sacrificial closure is sealingly applied to the outlet so as to preserve a future condition of sterility inside the pouch;

loading a plurality of provisional closed pouches to be sterilised on a transport device for collective transport;

performing a sterilisation of the transport group loaded with provisional closed pouches, by ionising radiation;

picking the sterilised provisional closed pouches from the transport device and sending the sterilised provisional closed pouches in succession to a sterile chamber;

for each sterilised closed pouch, making at least a portion of the tube provided with the sacrificial closure to pass through the sterile chamber;

during said passing through of the sterile chamber, separating the sacrificial closure from the tube, filling the sterilised open pouch and applying a tamper-proof cap to the tube to close the pouch;

collecting and setting aside the sacrificial closures.

10. An assembly comprising:

a transport device for collective transportation of flexible pouches;

a plurality of provisional closed non-filled pouches to be sterilised loaded on the transport device, wherein each provisional closed pouch to be sterilised comprises a container body having walls made of film, a straw sealingly applied to the container body and a sacrificial closure sealingly and reversibly applied to an inlet of a tube of the straw to close the tube, wherein the sacrificial closure is sealingly applied to the outlet to preserve a future condition of sterility inside the pouch.

11. The assembly according to claim 10, wherein the transport device is provided with fins suitable to support the pouch by engaging the pouch between the support surfaces of the straw.

12. The assembly according to claim 11, wherein the transport device is a section bar having prevalent extension along a sliding axis.

13. The assembly according to claim 12, wherein the pouches are slidable in the section bar along said sliding axis.

14. The assembly according to claim 13, wherein the fins cooperate with guide surfaces of the straw to guide the sliding of the pouch in the section bar.

15. The assembly according to claim 12, wherein the section bar has a delimited compartment delimited in part by a base, said compartment being suitable to accommodate at least a portion of the tube of the straw and the sacrificial closure applied to said tube.

16. A transport group comprising a plurality of simple transport surfaces, wherein each transport surface comprises a predefined number of assemblies according to claim 15, placed side by side at a same height and carrying provisional closed pouches to be sterilised arranged in a same direction, either all of the pouches standing, wherein the straw is arranged above and the pouch below; or all upside down, wherein the straw is arranged below and the pouch above, and wherein the transport surfaces are stacked.

17. A transport group comprising a plurality of dual transport surfaces, wherein each transport surface comprises a first level comprising a predefined number of assemblies according to claim 10, placed side by side at the same height, all carrying provisional closed pouches to be sterilised arranged in the same direction, either all of the pouches standing, wherein the straw is arranged above and the pouch below, or all of the pouches upside down, wherein the straw is arranged below and the pouch above, and a second level superimposed on the first level, comprising a predefined number of the assemblies, placed side by side and carrying the provisional closed pouches to be sterilised arranged in the direction opposite to direction of the first level, wherein all of the pouches are upside down or all of the pouches are standing, and wherein said transport surfaces are stacked.

* * * * *